United States Patent [19]

Solomon et al.

[11] Patent Number: 4,924,708
[45] Date of Patent: May 15, 1990

[54] METHOD FOR CALCULATING CRACK LENGTHS OF CONDUCTIVE SENSORS

[75] Inventors: Harvey D. Solomon; William R. Catlin, both of Schenectady, N.Y.

[73] Assignee: General Electric Company, Schenectady, N.Y.

[21] Appl. No.: 308,291

[22] Filed: Feb. 9, 1989

[51] Int. Cl.[5] .............................................. G01N 19/08
[52] U.S. Cl. ....................................................... 73/799
[58] Field of Search ........................... 73/799, 786, 810; 364/508

[56] References Cited

U.S. PATENT DOCUMENTS

| | | |
|---|---|---|
| 4,003,246 | 1/1977 | Cain . |
| 4,149,406 | 4/1979 | Russenberger ........................ 73/775 |
| 4,452,087 | 6/1984 | D'Antonio .............................. 73/786 |
| 4,535,629 | 8/1985 | Prine ................................. 364/508 X |
| 4,677,855 | 7/1987 | Coffin et al. ............................ 73/799 |

OTHER PUBLICATIONS

Catlin, Lord, Prater and Coffin, "The Reversing DC Electrical Potential Method", Automated Test Methods for Fracture and Fatigue Crack Growth, *ATSM*, STP877, Philadelphia, 1985, pp. 67–85.
Prater, Catlin and Coffin, "Application of the Reversing DC Electrical Potential Technique to Monitoring Crack Growth in Pipes", CRD Report No. 85CRD095, Jun. 1985.
Novak and Rolfe, "Modified WOL Specimen for $K_{iscc}$ Environmental Testing", *Journal of Materials*, vol. 4, pp. 701–728, 1969.
Tada, Paris and Irwin, "The Stress Analysis of Cracks Handbook", Del Research Corp., Hellertown, PA, 1973.
Klintworth, "Fatigue Crack Propagation in High Strength Low-Alloy Steel Using an Electrical Potential Method", M. Sc. Thesis, Imperial College of Science and Technology, University of London, Oct. 1977, pp. 79–80.
Editor: General Electric Company, "Electric Potential Drop Monitor", Operating and Instruction Manual.

*Primary Examiner*—Jerry W. Myracle
*Attorney, Agent, or Firm*—James E. McGinness; James C. Davis, Jr.; James Magee, Jr.

[57] ABSTRACT

A method is provided for measuring crack growth in a solid comprising a sensor utilizing potential or voltage drop measurements across a preformed and propagating crack. Preferably the sensor is representative of a structural component and is exposed to an aggressive environment like that in which the structural component operates. Measured voltage values are plotted versus a distance at which the voltages are measured by a plurality of pairs of probes, and intercept values are obtained and used in combination with previously measured crack lengths in calculating subsequent crack lengths of a propagating crack.

15 Claims, 5 Drawing Sheets

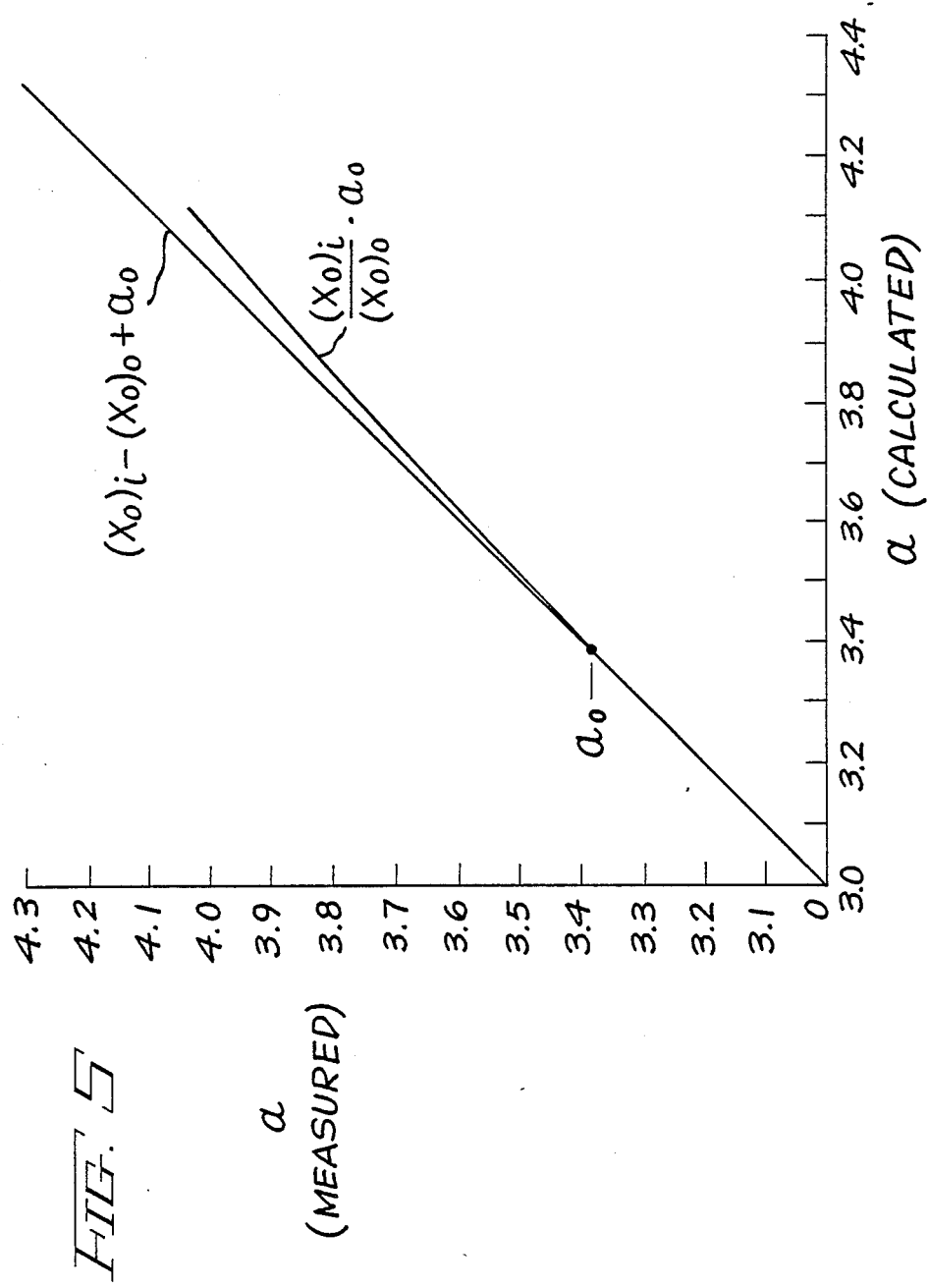

METHOD FOR CALCULATING CRACK LENGTHS OF CONDUCTIVE SENSORS

BACKGROUND OF THE INVENTION

1. Field of the Invention. The present invention relates to a method for measuring crack propagation within a sample in order to monitor damage to structural components.

2. Description of Related Art. It is well documented that when structural materials are exposed to particular aggressive service environments, and where the material is under steady or cyclic stress, the material will be susceptible to damage in the form of cracking. This type of damage is commonly referred to by names such as "stress corrosion cracking" or "corrosion fatigue". Many industries must cope with the possibility that stress corrosion cracking may occur in operating equipment. The nuclear industry in particular continues to encounter this problem where the structural materials operate under sustained or cyclic stress in the presence of high temperature water, such as in boiling water reactors.

At least in some respects, damage in the form of stress corrosion cracking, or other stress/environment-induced cracking, hereinafter referred to collectively as stress corrosion cracking, is of much greater concern in industry than damage such as that caused by uniform corrosion, which results in a predictable service life for components, as material failures due to stress corrosion cracking are many times not easily predicted and are generally significant in nature.

U.S. Pat. No. 4,677,855 issued to Coffin, Jr. et al, the subject matter of which is hereby incorporated by reference, sets our problems which industry in general, and the nuclear industry in particular, faces in attempting to predict the onset of or susceptibility of particular structural components to stress corrosion cracking. In general, the performance of structural components is predicted in advance from information on the expected loadings and resulting stress from these loadings. Although these predictions are sufficiently accurate to predict service performance, it has been found difficult to predict the lifetime of such performance due to the uncertainty in the environmental conditions and the influence thereof on the stress corrosion cracking which results therefrom.

An example of the uncertainty of lifetime predictions for structural materials is the stress corrosion cracking which has been found to occur in stainless steel piping used in the nuclear industry. Although designs for new plants attempt to compensate for this phenomenon, it is desirable to monitor and assess the extent of damage in plants which have been operating for a number of years to help predict their lifetimes and possibly extend their lifetime. Methods for assessing the state of damage have been directed toward monitoring the aggressive environment. In the case of boiling water reactors, the water chemistry is measured to determine factors such as resistivity, electrochemical potential, oxygen level and impurity levels. Such measurements are indirect. No direct measurement is made of the effect this water chemistry has on crack growth in the structural materials during plant service. Therefore, the extent to which the lifetime of the structural material is extended by varying operating conditions are unknown.

Methods for directly measuring crack growth in specimens removed from their environment have been disclosed over the years. These methods use a variety of monitoring systems including visual and voltage potential drop methods, such as that disclosed by Beevers, Editor, "The Measurement of Crack Length and Shape During Fracture and Fatigue", Engineering Materials Advisory Services, Limited, (1980). However, it was not until the method disclosed in the Coffin, Jr., et al. patent, that the industry was provided with the capability to accurately assess crack growth of plant structural components through voltage potential drop methods by disclosing a reasonably accurate way to relate voltage measurements to crack size.

OBJECTS OF THE INVENTION

Applicants have recently discovered an even more accurate method that may be employed and it is a principal object of the present invention to provide an improved, more accurate method for measuring and monitoring damage to structural components within their environments over extended periods of time.

A further object of the present invention is to provide a more accurate method for measuring the instantaneous and accumulated damage caused by cracking in structural components.

Another object of the present invention is to provide an improved method for calculating the crack growth in a sensor having a double-cantilever beam (DCB) geometry.

SUMMARY OF THE INVENTION

The above and other objects of the present invention and their attendant advantages are accomplished by providing a method for measuring crack growth within a solid wherein the solid, having a preformed crack, is exposed to an aggressive environment while applying a load to the solid sufficient for the crack to grow. A current is passed through the solid to establish a voltage drop across the crack. This voltage is measured by at least two pairs of probes, the two members of each pair of probes being positioned on opposite sides of the crack at equal, known distances from the mouth of the crack. The measured voltage across each pair is plotted versus the distance from the crack mouth of each probe pair. A "best fit" curve or straight line of voltage versus the distance of the probe pairs from the crack mouth is passed through these points and extrapolated to obtain the x-intercept or distance intercept of the line at the axis where voltage = 0. X-intercept values thus obtained which are associated with an initial known crack length and subsequent crack lengths are used to calculate, according to relationships developed in the present invention, the length of a propagating crack.

The measurement technique and method of the present invention may be used to assist in determining or estimating the damage occurring in structural components exposed to stress and to aggressive environments. In such a case the solid would take the form of a sensor having a preformed crack, the sensor would be disposed in the aggressive environment and the crack would be supplied with a stress intensity at the crack tip which correlates to a stress intensity which the structural component experiences under operating conditions. Alternatively, the method of the present invention may be employed in general materials research in identifying and predicting relative susceptibility of materials to stress corrosion cracking in various environments.

BRIEF DESCRIPTION OF THE DRAWINGS

FIG. 5 depicts the correlation between crack length "a" as actually measured and the crack length "a" as calculated using the method of the present invention compared with the "as calculated" crack length according to the method disclosed in the Coffin, Jr., et al. patent.

DETAILED DESCRIPTION OF THE INVENTION

This invention is directed to an improved method for measuring crack growth within a solid. Embodiments of this invention can be used to determine damage to structural components within their environment due to stress corrosion cracking. This is accomplished by measuring and monitoring the electric potential drop across a preformed crack within a solid material of interest, herein referred to as a "sensor". When a current is caused to flow through the sensor perpendicular to the crack, the potential difference between two points located on opposite sides of the crack will increase as the size of the crack increases. Measurement of the electric potential will provide information as to the instantaneous damage as well as the accumulated damage to the sensor in the form of crack growth.

Crack growth is preferably measured in a solid material of interest or sensor. The solid must be electrically conductive, such as carbon or alloy steel, nickel and nickel based alloys, titanium and its alloys and nuclear structural materials such as austenitic stainless steels, Inconel TM and the like. This is necessary to obtain measurements of the electric potential across the preformed crack. In the preferred embodiments of this invention, the sensor provides information which reflects on the condition of a particular structural component of interest. To achieve this purpose, it is preferable to manufacture this sensor from the same material with the same process history as the structural component of interest. The size and shape of the sensor can vary widely. Certain sizes and shapes may be preferred to enhance compactness, durability, sensitivity, simplicity of installment or flexibility.

The preformed crack within the solid is of a known length designated herein as $a_o$. This preformed crack defines the site where electric potential measurements are taken. Therefore, it is desirable to position the crack at a location on the sensor convenient for taking electric potential measurements at multiple points. The size and shape of the preformed crack can vary widely; however, the cracks cannot be of a size so as to separate the sensor into two sections. The crack is defined as possessing a mouth and a tip. The "mouth of the crack" is defined herein as the point or line of action of load application. The "crack tip" is the leading edge of the crack. The "length" of the crack is defined herein as the distance from the mouth of the crack to the crack tip. As indicated above, the initial length of the preformed crack is defined herein as $a_o$.

Figure 1:
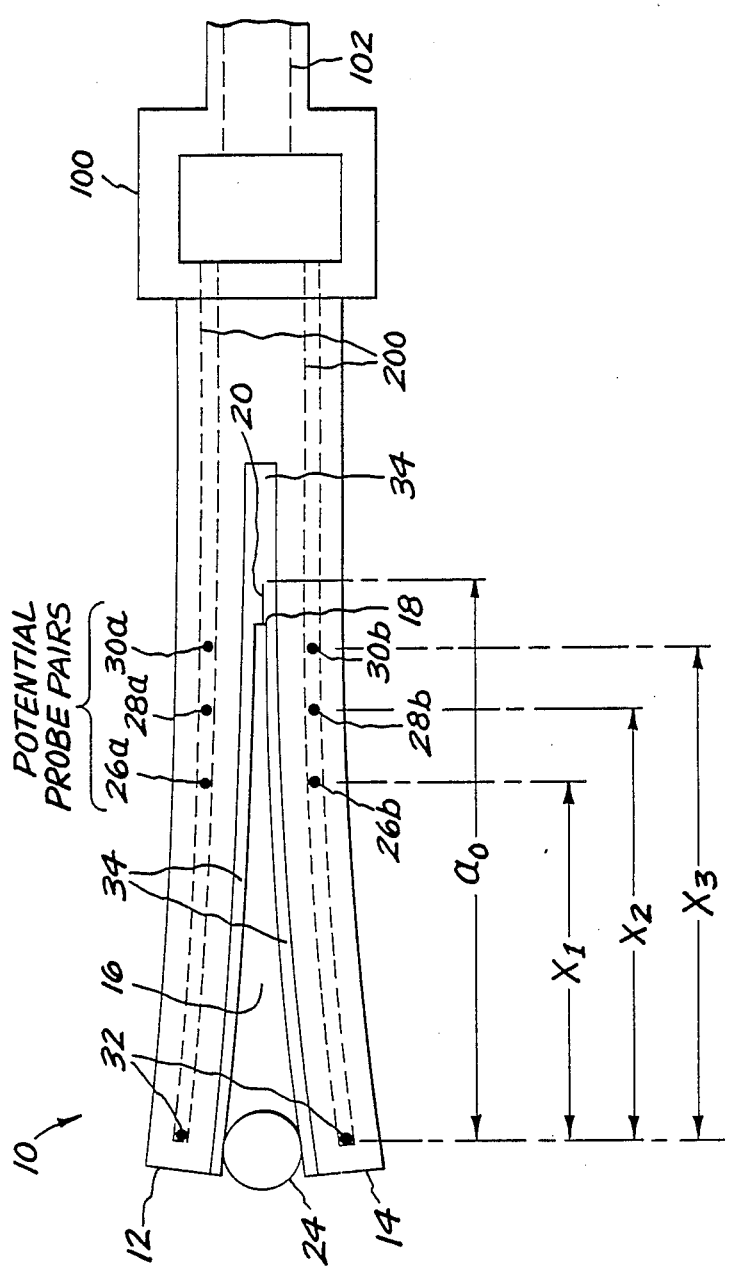
FIG. 1 is a substantially schematic representation of a sensor, having a double cantilever beam geometry, which is an example of a type of sensor which may be used in the method of the present invention.

Although the sensor size, crack size and crack location can vary widely, the configuration of the sensor preferably permits a load of sufficient magnitude to be applied to the crack to provide a crack tip stress intensity factor that will allow the crack to grow at an appropriate rate. In addition, it is preferable for the configuration of the sensor to permit measurement of the electric potential at multiple points along the crack. A configuration which permits a load of sufficient magnitude to be conveniently applied is that of the sensor 10 shown in FIG. 1 having a "double cantilever beam" or DCB geometry. This geometry is defined herein and depicted schematically in FIG. 1 as having two parallel arms (beams) 12, and 14 joined at one end and separated at the other. A slot or deep notch 16 separates the arms, and the base of this notch is referred to as the notch root 18. The preformed crack 20 is preferably positioned at the notch root. This compact shape provides high flexibility and high sensitivity. This configuration permits a number of measurements to be taken at various positions along the two beams 12, 14 since the effective crack length is extended along these beams. In addition, if the load remains constant, the stress intensity factor at the crack tip increases as the distance between the crack tip and the point of the load increases. Therefore, the long length of the sensor permits the threshold crack tip stress intensity to be obtained at low load levels. Loads sufficient for the crack to grow can be obtained by simply placing a wedge 24 between the two beams 12, 14.

The level of stress at the tip of a sharp crack in a solid is characterized by the stress intensity factor. For the preformed crack to grow it must experience a minimum or threshold stress intensity factor at the crack tip. U.S. Pat. No. 4,677,855, the subject matter of which is hereby incorporated by reference describes how the stress intensity factor for a sensor of a particular geometry is determined. That patent further includes a comprehensive discussion of the use of such sensors for predicting failure and monitoring of crack growth in structural components.

For monitoring stress corrosion cracking in aggressive environments, an active load or a fixed displacement must be applied to the sensor. The means for applying a fixed displacement to cause the preformed crack to grow can be the aforementioned wedge 24 forced within the notch to expand the crack. Other means are also suitable, such as a clamp, bolt or similar means which expands the crack. The means for applying a fixed displacement must be comprised of a material which is electrically non-conductive and it is preferred that such material have a thermal coefficient of expansion which matches that of the sensor material. This helps maintain a nearly constant stress intensity factor at the crack tip under changing temperatures. Where the sensor is to be placed within an aggressive environment, it is essential that the material utilized to apply the fixed displacement be resistant to such aggressive environments.

In the preferred embodiments of this invention, the sensor, having a preformed crack is placed within an aggressive environment. The term "aggressive environment", as used herein, refers to those environments attack the material or which the sensor is comprised, such attack being of sufficient magnitude to enhance the growth of the preformed crack. When monitoring the damage to a structural component, the sensor is placed within the same environment as the structural component. The sensor then experiences the same changing environmental conditions as these structural components. Conventional methods and devices can be used to support the sensor in these environments.

Crack growth in the present invention is preferably monitored by measuring a potential or voltage across pairs of probes disposed along beams 12, and 14, and using such measured voltages, as well as the initial parameters in calculating a crack length. Calculated crack lengths may further advantageously be plotted as a function of time in order to assess a rate of crack growth.

Voltage is measured across the crack by multiple pairs of probes. At least two pairs of probes are required to perform this process; however, at least three pairs of probes 26a,b; 28a,b; and 30a,b; are preferred for accurate measurement of the crack growth. Each pair of probes is positioned at a different distance from the mouth of the crack, indicated in FIG. 1 as $X_1$, $X_2$, and $X_3$. The two members of each pair are positioned on opposite sides of the crack, preferably an equal distance from the plane of the crack. The two members of each pair are also equi-distant from the mouth of the crack, i.e., they are the same distance from the leads 32 which supply a current to the sensor. U.S. Pat. No. 4,677,855 discloses at least one example of probe positioning suitable for use in the present invention.

The potential difference across the preformed crack can be detected by conventional means capable of receiving a voltage across a pair of probes on a conductive material. The probes can be simple contacts, screws, welds and the like where a conductive lead, such as a wire, cable, bus, etc. is affixed to the sensor. These conductive leads are affixed to the sensor in a manner which permits electrical conductance to a voltage measuring device, such as a voltmeter or an analog/digital converter.

As indicated above, in the preferred configuration for a sensor, sensor 10 is of a double cantilever beam geometry. Preformed crack 20 is positioned at the notch root 18 of the double cantilever beam. Side grooves 34 are located on both beams 12, 14 on the portions of the beams facing one another. The side grooves reduce the thickness of the portion of the beams facing each other and reduce the thickness of the region in which the preformed crack is located. The sensor is supported in the aggressive environment by pressure coupling 100. Channel 102 provides access to channels (or holes) 200, both of which provide pathways for the conductive leads attached to the probe pairs and to conductive leads which preferably supply a d.c. potential to the sensor. The reversing direct current is supplied at points 32 and the effective initial length of the crack is indicated by line $a_o$. Probe pairs 26a,b; 28a,b; and 30a,b; detect the voltage across the crack. Wedge 24 applies a static load on the crack 20, providing the desired crack tip stress intensity factor.

It is preferable to measure the value of the potential difference across the probes continuously; however, intermittent measurements of the potential difference are acceptable and do provide useful information as to crack growth. It is desirable to measure the potential difference as accurately as possible so as to enhance the eventual determination of crack length and growth. U.S. Pat. No. 4,677,855 discloses a detailed approach to making accurate measurements of potential differences, and such an approach would be suitable for use in connection with the present invention. Other measurement approaches may also prove to be suitably accurate for use.

Figure 2:
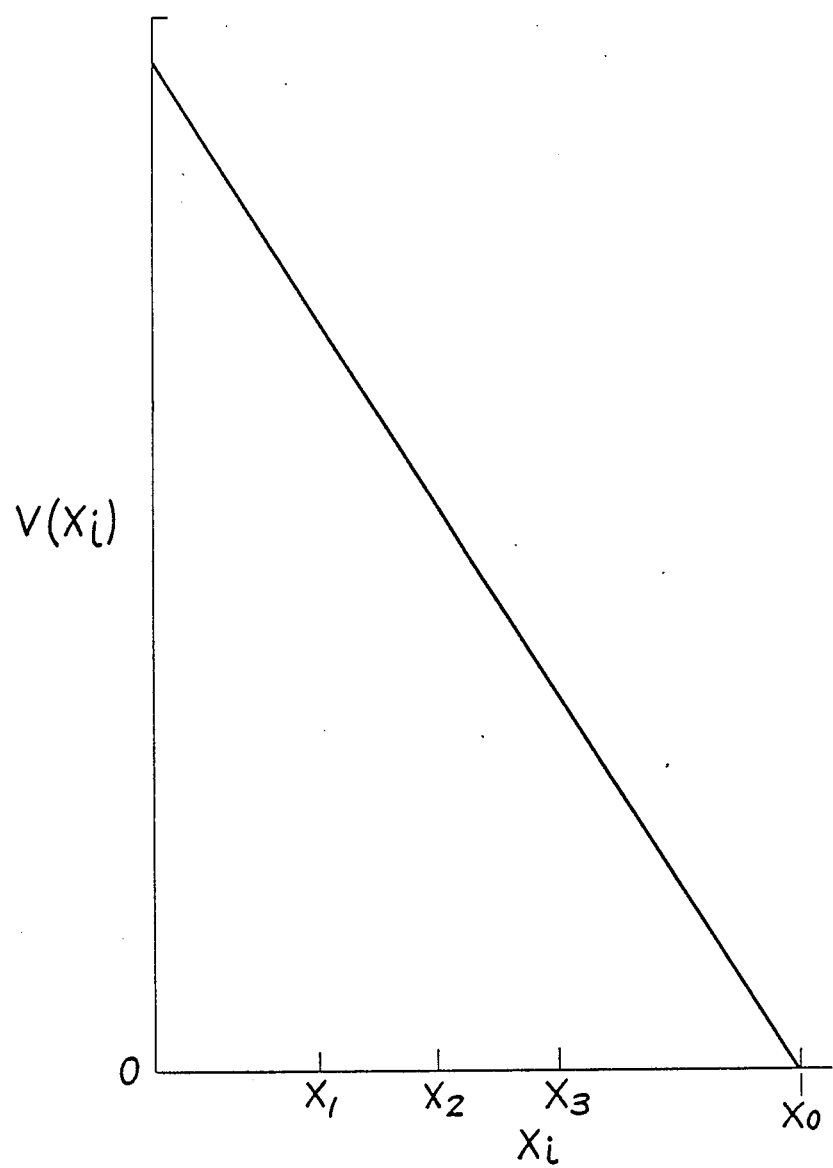
FIG. 2 is a sample plot of the relation between a potential V and positions $X_i$ where the potential is measured.

As shown schematically in the graph of FIG. 2, the measured voltage across each pair of probes may be plotted against the depth or measuring distance of the probes from the mouth of the crack ($X_1$, $X_2$, $X_3$) by performing a least squares curve fit, or by other means of approximating a straight line extending through the points. The slope of this line or curve, such as that depicted in FIG. 2, varies as a function of the current applied to the sensor, the sensor resistivity, and the sensor geometry. Of primary interest in the plot of potential as a function of measuring distance in crack growth calculations is the x-intercept value, $X_o$, the x-intercept being where potential or voltage, V, is equal to zero (V=0).

Because the voltage measured across a particular pair of probes will increase as the crack length increases, the curve will shift, further causing the x-intercept value to change as the crack length, a, increases under the applied load. The x-intercept ($X_o$) varies as a function of total crack length, a, i.e., the arm or beam length plus the starter (preformed) crack, plus the propagating fatigue crack length. This function $X_o(a)$ may be expressed generally as a linear relation:

$$X_o = Na + D \qquad [1]$$

wherein N and D are constants, $X_o$ being the x-intercept value of the potential-versus-measuring distance curve for a particular total crack length (a). Associated crack lengths and x-intercept values derived from the above relation will be identified herein as, for example, $a_o$, $(X_o)_o; a_i, (X_o)_i;$ and generally as $a_i, (X_o)_i$.

As a starting point for discussing the improvement provided by the method of the present invention, the method disclosed in U.S. Pat. No. 4,677,855, will be briefly discussed and compared. The formula expressed in that patent which was used for calculating the length (depth) of the crack as the crack propagated through the sample took the form:

$$a_2 = \left[ \frac{I_2}{I_o} \right] a_o \qquad [2]$$

In this formula, $a_o$ represents an initial crack length $I_o$ represents an associated x-intercept value (equivalent to $(X_o)_o$ in the present application) of a plot of potential versus measuring distance, and $I_2$ represents an x-intercept value derived from the potential measurement as a function of measuring distance when the crack has propagated from the initially measured crack length $a_o$ to an unmeasured crack length $a_2$.

This formula [2] is derived using linear relation [1] above, but relies on an assumption that constant D in equation [1] is equal to zero (D=0). While formula [2] above provides a reasonably accurate method of calculating a subsequent crack length $a_i$, recent work leading to the present invention has led to the development of an improved, more accurate method for calculating $a_i$ values from known parameters. It has been shown in experiments conducted in connection with the present invention that the constant D in equation [1] above does not equal zero in all cases, and therefore, the use of formula [2] to calculate the length $a_i$ of the propagating crack will produce inaccurate results in many instances.

In accordance with the present invention, wherein it has been recognized that constant D may not be assumed to equal zero, a relationship or formula directed to calculating the crack length $a_i$ may be derived from equation [1] as follows:

$$(X_o)_o - Na_o = D = (X_o)_i - Na_i \quad [3]$$

and solving for $$a_i = a_o + \frac{(X_o)_i - (X_o)_o}{N} \quad [4]$$

This equation [4] is not, however, capable of being used in sensors where N has not previously been determined. In a situation where N is unknown, in addition to the initial, direct measurement of crack length $a_o$, a second direct measurement of crack length $a_1$ is made, and an associated x-intercept value $(X_o)_1$ may be determined from the potential or voltage measurements of the probes, these values being substituted in equation [4] for $a_i$ and $(X_o)_i$, and the equation solved for n as follows:

$$a_1 = a_o + \frac{(X_o)_1 - (X_o)_o}{N} \quad [5]$$

and thus, $$N = \frac{(X_o)_1 - (X_o)_o}{a_1 - a_o} \quad [6]$$

Substituting this expression for N into equation [4], the more accurate equation, according to the present invention, for calculating $a_i$ is obtained:

$$a_i = \frac{[(X_o)_i - (X_o)_o](a_1 - a_o)}{(X_o)_1 - (X_o)_o} + a_o \quad [7]$$

or, stated another way, $$a_i = a_o \left[ \frac{(X_o)_1 - (X_o)_i}{(X_o)_1 - (X_o)_o} \right] + a_1 \left[ \frac{(X_o)_i - (X_o)_o}{(X_o)_1 - (X_o)_o} \right] \quad [8]$$

Where N is susceptible of being determined prior to the commencement of a crack measurement exercise, equation [4] is capable of being used, which simplifies the method by eliminating the requirement to make the second crack measurement $a_1$.

A digital computer can calculate the values for the intercepts and perform the functions on these values to obtain data which corresponds to the length of the crack. This data may be communicated to the user by conventional means, such as a visual recorder or by acoustic warning signals. The data may also be communicated to an automatic control mechanism and/or stored for subsequent analysis and interpretation. In any event, where certain steps in the method of the present invention are discussed in terms of "approximating", "extrapolating", and the like, it is to be recognized that a computer may be employed to accomplish some or all of such method steps.

The following example is provided to illustrate an embodiment of this invention. It is not intended to limit the scope of the claimed invention to the embodiment described.

EXAMPLE

Figure 3:
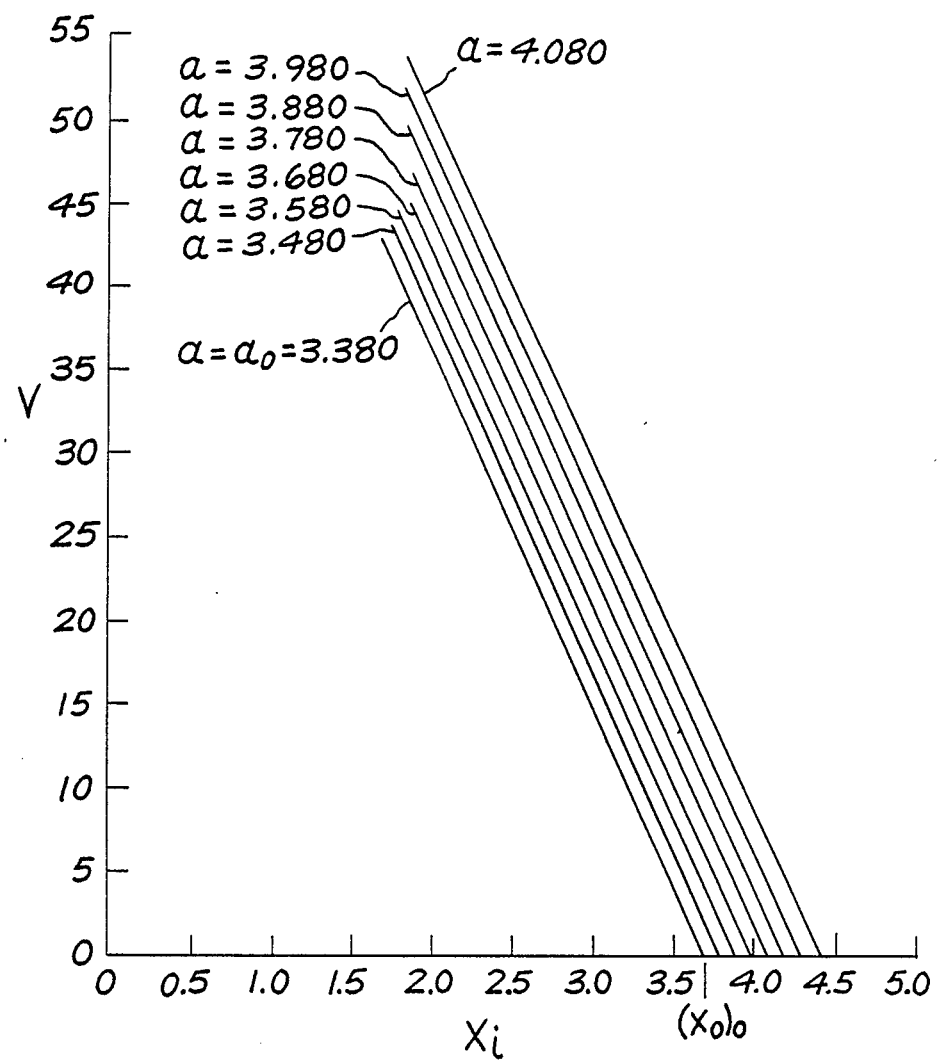
FIG. 3 is a graph displaying results of examples of measured potential V as a function of the position or distance from the mouth of the crack $X_i$ where the potential is measured, further displaying the effect of increases in crack length on the relationship. Each curve represents the results for a different crack length, "a".

In an example demonstrating the improved accuracy of the method of the present invention, a DCB sensor was employed, and the set of curves in FIG. 3 were generated. FIG. 3 shows the potential or voltage measured as a function of the distance $X_i$ of pairs of probes from the mouth of the crack (see, e.g., FIG. 1). Seven pairs of probes were employed in this particular example. In the DCB sensor, electromachining was employed to elongate a starter notch. $V(X_i)$ was measured and the crack was caused to propagate to a new crack length and a new set of $V(X_i)$ measurements was made. Direct optical measurement of the crack length at each measurement interval was also made in order to compare calculated values with actual measured values.

The seven pairs of probes were equally spaced at distances ranging from 2.0 to 3.5 inches from the crack mouth. The potential or voltage data obtained was plotted and the data points associated with each new crack length $a_i$ were subjected to a least squares fit in order to extrapolate potential V to V=o and $X_i=(X_o)_i$. Table I presents the $(X_o)_i$ values obtained alongside the associated crack lengths $a_i$ which were directly (optically) measured in the experiment.

TABLE I

| | $a_i$ (in.) | | $(X_o)_i$ |
|---|---|---|---|
| $a_0$ | 3.380 | $(X_o)_o$ | 3.6928 |
| $a_1$ | 3 480 | $(X_o)_1$ | 3.7901 |
| $a_2$ | 3.580 | $(X_o)_2$ | 3.8545 |
| $a_3$ | 3.680 | $(X_o)_3$ | 3.9973 |
| $a_4$ | 3.780 | $(X_o)_4$ | 3.0983 |
| $a_5$ | 3.880 | $(X_o)_5$ | 3.1968 |
| $a_6$ | 3.980 | $(X_o)_6$ | 4.2935 |
| $a_7$ | 4.080 | $(X_o)_7$ | 4.3894 |

Figure 4:
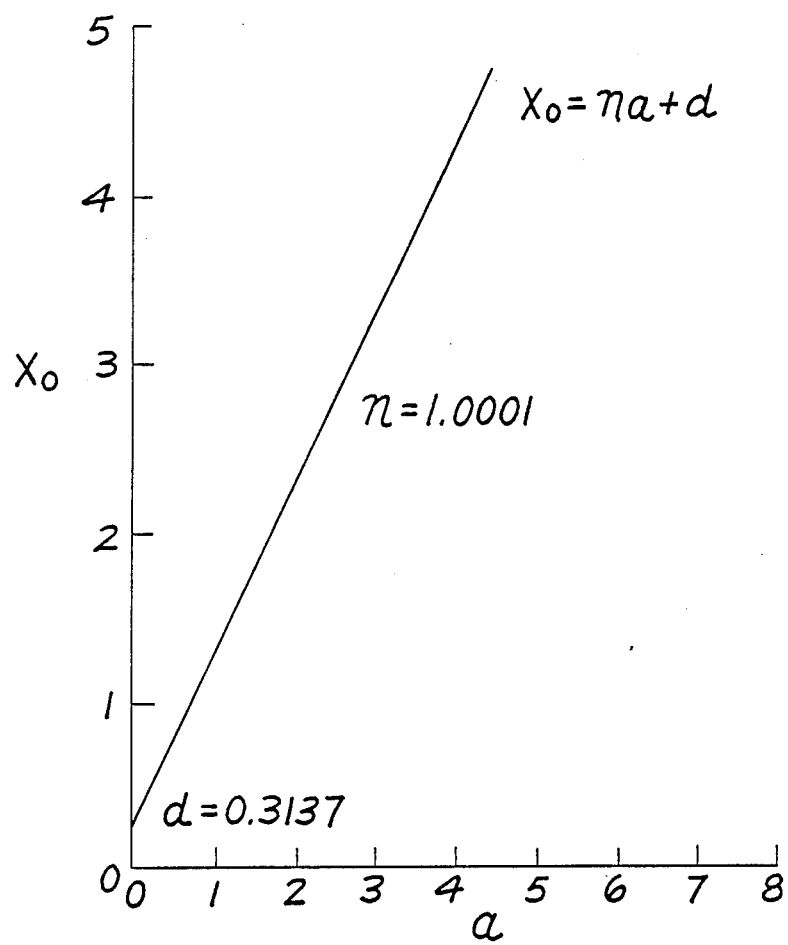
FIG. 4 is a graph showing the change in the x-intercept shown in FIG. 3 (potential V versus measurement position $X_i$) as a function of measured crack length "a".

FIG. 4 is a graph of the x-intercept values plotted as a function of the measured crack lengths, the data presented in Table I. It is to be recognized that values for constants N and D for the generalized equation [1] may be obtained from this plot for this particular sensor example, N being the slope of the line fitted to the data points, and D being the y-intercept value (i.e., a=o). It can thus be seen that D does not equal 0, but rather, in this instance, D=0.3137. Further, the slope, N, of this line is equal to 1.0001, or essentially N=1.

FIG. 5 is a graph which compares the accuracy of the method of calculating a subsequent crack length $a_i$ by the method according to the present invention with the directly measured crack length $a_i$ in the example, as well as with the formula disclosed in U.S. Pat. No. 4,677,855, i.e., formula [2] identified previously in the specification. In this particular example, where N has been determined to equal unity, the plot of points according to the method of the present invention may be more easily calculated using equation [4], rather than the more general equations [7] and [8]. With N=1, equation [4] reduces to:

$$a_i = a_0 + (X_o)_i - (X_o)_o$$

Table II below presents the data points plotted in FIG. 5 to further facilitate comparison.

TABLE II

| | a (measured) | $a_o + (X_o)_i - (X_o)_o$ | $\frac{(X_o)_i}{(X_o)_o} \cdot a_o$ |
|---|---|---|---|
| $a_0$ | 3.380 | 3.380 | 3.380 |
| $a_1$ | 3.480 | 3.4773 | 3.469 |
| $a_2$ | 3.580 | 3.5817 | 3.528 |
| $a_3$ | 3.680 | 3.6845 | 3.659 |
| $a_4$ | 3.780 | 3.7855 | 3.751 |
| $a_5$ | 3.880 | 3.8840 | 3.841 |
| $a_6$ | 3.980 | 3.9807 | 3.930 |
| $a_7$ | 4.080 | 4.0766 | 4.018 |

Thus, it can be seen from FIG. 5 and Table II that a much closer correlation between the crack length as calculated by the method of the present invention and the crack length as actually measured is attained.

It will be obvious to those skilled in the art that variations of the above embodiments are possible without departing from the full scope and true spirit of this invention. It is therefore intended that such variations be included within the scope of this invention, which is defined by the appended claims.

We claim:

1. A method for measuring crack growth within a solid having a preformed crack and a crack mouth which comprises the steps of:
    applying a current to the solid to produce a potential field within said solid;
    making a first measurement of an initial crack length ($a_o$);
    measuring a first set of potentials ($V_o$) across the crack using at least two pairs of probes positioned at predetermined distances from said crack mouth along a length of the crack, the two probes from each pair of probes being positioned on opposite sides of the crack at an equivalent distance from the mouth of the crack;
    extrapolating an intercept value $(X_o)_o$ associated with said initial crack length ($a_o$), where said potential V=0, from a plot of said first set of potentials ($V_o$) measured as a function of said predetermined distances of the pairs of probes from said crack mouth;
    making a measurement of a subsequent crack length ($a_1$);
    measuring a second set of potentials ($V_1$) across the crack using the pairs of probes positioned at predetermined distances from said crack mouth;
    extrapolating an intercept value $(X_o)_1$ associated with said crack length ($a_1$), where said potential V=0, from a plot of said second set of potentials ($V_1$) measured as a function of said predetermined distances of the pairs of probes from said crack mouth;
    measuring a subsequent set of potentials ($V_i$) across the crack, said set of potentials ($V_i$) being associated with a subsequent crack length ($a_i$), using the pairs of probes positioned at predetermined distances from said crack mouth;
    extrapolating an intercept value $(X_o)_i$ associated with said subsequent crack length ($a_i$), where said potential V=0, from a plot of said subsequent set of potentials ($V_i$) measured as a function of said distances of the pairs of probes from said crack mouth; and calculating said subsequent crack length ($a_i$) from the equation $$a_i = a_o\left[\frac{(X_o)_1 - (X_o)_i}{(X_o)_1 - (X_o)_o}\right] + a_1\left[\frac{(X_o)_i - (X_o)_o}{(X_o)_1 - (X_o)_o}\right].$$

2. A method as defined in claim 1 wherein a load is applied to the crack sufficient to cause the crack to grow.

3. A method as defined in claim 2 wherein the solid comprises a sensor having a double beam cantilever geometry.

4. A method for determining a crack length in a double cantilever beam sensor having a preformed crack comprising the steps of:
    measuring an initial crack length $a_o$;
    applying a current to the sensor to produce a potential field within the sensor;
    positioning at least two pairs of probes on said sensor, the two probes from each pair of probes being positioned on opposite sides of said preformed crack at an equal distance from a mouth of said crack;
    measuring voltages (V) across said preformed crack using the pairs of probes;
    approximating a curve with said measured voltages (V) across the pairs of probes versus the distance, plotted on an x-axis, of the pairs of probes from said mouth of aid crack;
    extrapolating said curve to obtain an x-intercept value, where V=0, associated with said initial crack length $a_o$;
    measuring a further crack length $a_1$;
    measuring voltages ($V_1$) across said crack using the pairs of probes;
    approximating a curve with said measured voltages ($V_1$) across the pairs of probes versus the distance, plotted on said x-axis, of the pairs of probes from aid mouth of said crack;
    extrapolating said curve to obtain an x-intercept value $(X_o)_1$, where V=0, associated with said crack length $a_1$;
    measuring subsequent voltages ($V_1$) across said crack using the pairs of probes;
    approximating a subsequent curve with said subsequent measured voltages ($V_1$) across the pairs of probes versus the distance, plotted on said x-axis, of the pairs of probes from said mouth of said crack;
    extrapolating said subsequent curve to obtain a subsequent x-intercept value $(X_o)_i$, where V=0; and
    calculating a subsequent crack length $a_i$ associated with said x-intercept value $(X_o)_i$ using the relationship:

$$a_i = a_o\left[\frac{(X_o)_1 - (X_o)_i}{(X_o)_1 - (X_o)_o}\right] + a_1\left[\frac{(X_o)_i - (X_o)_o}{(X_o)_1 - (X_o)_o}\right].$$

5. A method as defined in claim 4 wherein said approximation of said curves is accomplished using a least-squares fit calculation.

6. A method as defined in claim 5 wherein from three to seven pairs of probes are positioned across the crack to measure said voltages.

7. A method for monitoring crack growth in a sensor having a preformed crack comprising the steps of:
    measuring an initial crack length $a_o$;

applying a current to the sensor to produce a potential field within the sensor;

positioning at least two pairs of probes on said sensor, the two probes from each pair of probes being positioned on opposite sides of said preformed crack at an equal distance from a mouth of said crack;

measuring a first set of voltages (V) across said preformed crack using the pairs of probes;

approximating a straight line function with said first set of measured voltages (V) across the pairs of probes versus the distance, plotted on an x-axis, of the pairs of probes from said mouth of said crack;

extrapolating said straight line function to obtain an x-intercept value $(X_o)_o$, where $V=0$, associated with said initial crack length $a_o$;

measuring a further crack length $a_1$;

measuring a second set of voltages $(V_1)$ across said crack using the pairs of probes;

approximating a second straight line function with said second set of measured voltages $(V_1)$ across the pairs of probes versus the distance, plotted on said x-axis, of the pairs of probes from said mouth of said crack;

extrapolating said second straight line function to obtain an x-intercept value $(X_o)_1$, where $V=0$, associated with said crack length $a_1$;

monitoring said voltages across said crack using the pairs of probes to measure subsequent voltage changes;

obtaining further x-intercept values $(X_o)_i$ by approximating subsequent straight line functions of said subsequent voltage changes across the pair of probes versus the distance, plotted on said x-axis, of the pairs of probes from said mouth of said crack, and extrapolating said subsequent straight line functions to said x-axis, where $V=0$; and calculating subsequent crack lengths $a_i$ associated with said x-intercept values $(X_o)_i$, using the relationship:

$$a_i = a_o \left[ \frac{(X_o)_1 - (X_o)_i}{(X_o)_1 - (X_o)_o} \right] + a_1 \left[ \frac{(X_o)_i - (X_o)_o}{(X_o)_1 - (X_o)_o} \right].$$

8. A method as defined in claim 7 wherein said sensor is a double cantilever beam sensor.

9. A method as defined in claim 8 wherein said sensor is exposed to an operating environment and wherein said crack growth monitored is used to estimate crack growth damage of an equipment component operating in said environment.

10. A method as defined in claim 9 wherein said sensor is of the same composition as the equipment component.

11. A method as defined in claim 10 wherein a load is applied to said sensor to provide a crack tip stress intensity factor which is about equal to an anticipated stress intensity factor experienced by said equipment component.

12. A method for determining a crack length in a sensor having a preformed crack, and having at least two pairs of probes, the two probes of each pair of probes being positioned on opposite sides of said preformed crack at an equal distance from a mouth of the crack, and wherein a slope N of a curve of voltages measured by said pairs of probes plotted as a function of distance of said pairs of probes from said mouth of said crack is known, the method comprising the steps of:

measuring an initial crack length $a_o$;

applying a current to said sensor to produce a potential field within the sensor;

measuring voltages (V) across said preformed crack using the pairs of probes;

approximating a straight line function with said measured voltages (V) across the pairs of probes versus the distance, plotted on an x-axis, of said pairs of probes from said mouth of said crack;

extrapolating said straight line function to obtain an x-intercept value $(X_o)_o$, where $V=0$, associated with said initial crack length $a_o$;

measuring subsequent voltages $(V_i)$ across said crack using the pairs of probes;

obtaining further x-intercept values $(X_o)_i$ by approximating straight line functions with said measured voltages $(V_i)$ across the pairs of probes versus the distance, plotted on said x-axis, of said pairs of probes from said mouth of said crack, and extrapolating said straight line functions to said x-axis to obtain x-intercept values $(X_o)_i$, where $V=0$; and calculating subsequent crack lengths $a_i$ associated with said $(X_o)_i$ values, using the relationship $$a_i = a_o + \frac{(X_o)_i - (X_o)_o}{N}.$$

13. A method as defined in claim 12 wherein a load is applied to the crack sufficient to cause the crack to grow.

14. A method as defined in claim 13 wherein said slope N is substantially equal to one (N=1).

15. A method as defined in claim 14 wherein said sensor is of a double cantilever beam geometry.

* * * * *